United States Patent
Di Modugno et al.

(10) Patent No.: US 9,131,679 B2
(45) Date of Patent: Sep. 15, 2015

(54) HERBICIDAL COMPOSITION

(71) Applicant: LAMBERTI SpA, Albizzate (Varese) (IT)

(72) Inventors: Rocco Di Modugno, The Woodlands, TX (US); Dario Fornara, Novara (IT); Giovanni Floridi, Novara (IT); Giuseppe Li Bassi, Gavirate (IT)

(73) Assignee: LAMBERTI SPA, Albizzate (VA) (IT)

( * ) Notice: Subject to any disclaimer, the term of this patent is extended or adjusted under 35 U.S.C. 154(b) by 0 days.

(21) Appl. No.: 14/180,073

(22) Filed: Feb. 13, 2014

(65) Prior Publication Data

US 2015/0223448 A1 Aug. 13, 2015

(51) Int. Cl.
- *A01N 65/00* (2009.01)
- *A01N 57/18* (2006.01)
- *A01N 25/02* (2006.01)
- *A01N 57/20* (2006.01)

(52) U.S. Cl.
CPC .............. *A01N 25/02* (2013.01); *A01N 57/20* (2013.01)

(58) Field of Classification Search
None
See application file for complete search history.

(56) References Cited

U.S. PATENT DOCUMENTS

| | | | | |
|---|---|---|---|---|
| 2,310,679 A | * | 2/1943 | Keiser et al. | ............ 554/80 |
| 3,799,758 A | | 3/1974 | Franzus | |
| 5,385,750 A | | 1/1995 | Aleksejczyk et al. | |
| 8,211,832 B2 | | 7/2012 | Stickler et al. | |

FOREIGN PATENT DOCUMENTS

| | | |
|---|---|---|
| WO | WO 2005/087785 A3 | 9/2005 |
| WO | WO 2011/000880 A2 | 1/2011 |

* cited by examiner

*Primary Examiner* — Alton Pryor
(74) *Attorney, Agent, or Firm* — Mossman, Kumar & Tyler PC

(57) ABSTRACT

Ethoxylated phospholipid-enriched soybean oil as an effective adjuvant in herbicidal compositions and method for killing or controlling the growth of weeds which comprises applying on the fields a herbicidal composition containing glyphosate and the ethoxylated phospholipid-enriched soybean oil.

7 Claims, No Drawings

HERBICIDAL COMPOSITION

BACKGROUND OF THE INVENTION

1. Field of the Invention

The invention relates to an adjuvant for herbicidal compositions. This invention particularly relates to herbicidal compositions containing an adjuvant and an herbicide.

2. Background of the Art

Glyphosate (N-(phosphonomethyl)glycine in acid or salt form) is a known, effective herbicide. Glyphosate is the most widely used non-selective systemic herbicide that is used to control a broad spectrum of annual and perennial weeds. It works by inhibiting 5-enolpyruvylshikimate-3-phosphate synthase (EPSPS), an enzyme of the aromatic acids biosynthetic pathway, thus preventing the synthesis of essential aromatic amino acids that are needed for protein biosynthesis.

The acid form of glyphosate is poorly soluble in water and for this reason glyphosate is typically commercialized as a salt that exhibits sufficiently high solubility in water to provide concentrated herbicidal formulations that are diluted by the end-user on field. For example, aqueous concentrated formulations are known of the isopropylamine salt (IPA), the monoethanolamine (MEA) salt and of the potassium salt of glyphosate.

Glyphosate is usually applied by the end user as a diluted spray aqueous solution. Diluted spray aqueous solutions of glyphosate typically include at least one surfactant. The presence of a surfactant is highly desirable since surfactants reduce the interface tension between the aqueous spray and the material (foliage) to be treated (i.e. they improve wetting), thus favoring the spreading of droplets on the treated surface, the penetration of the active ingredient into the materials and the overall bioefficacy of the solution.

Because of this favorable behavior, a great variety of surfactants have been described to act as "adjuvants" in glyphosate formulations. By way of example, U.S. Pat. No. 3,799,758, which is fully incorporated herein by reference, includes in the herbicidal formulation a surface-active adjuvant, comprising, among others: alkyl benzene sulfonates or alkyl naphthalene sulfonates, sulfated fatty alcohols, amines or acid amines derivatives, esters of sodium sulfosuccinate, sulfonated vegetable oils and ethoxylated alkyl amine, the latter being preferred in the majority of the commercial formulations due to its low cost and reasonable efficiency.

Alkyl amine ethoxylates, and in particular ethoxylated tallow amine, are most frequently used as adjuvants with pesticides, in particular as adjuvants for glyphosate. Various other alkyl amine based surfactants have been described to provide excellent bioefficacy to glyphosate.

Among surfactants which can be used for the afore mentioned purpose, aliphatic alkylpolyglycoside derivatives have also been known for a long time. These materials offer several advantages due to their low toxicity and good biodegradability, especially if compared with the ethoxylated fatty amines, which create concern for their aquatic toxicity.

WO 05/087785 discloses an improved process for making ethoxylates of alkyloligoglycosides and their use as adjuvants, in particular for glyphosate-based herbicides.

WO 2011/000880 describes stable aqueous herbicide concentrate composition containing potassium, ammonium or isopropylamine salts of glyphosate and anionic esters of alkyl polyglycosides containing a salified sulfonic acid group.

Lecithin based adjuvants for glyphosate are also known from U.S. Pat. No. 8,211,832. However, the use of common surfactants in glyphosate-based formulations has still some problems. When the surfactant is added to a concentrated aqueous glyphosate salt solution, before dilution, segregation of the components may occur, such phenomenon being known in the art as salting-out. In practice, the solution initially becomes turbid and this phenomenon is followed by the separation of the surfactant agent originally dissolved in water which floats on the surface, while the saline solution precipitates towards the bottom. For example, most classes of non-ionic surfactants, including polyethoxylated alcohol, are not compatible with high ionic strength solutions, such as concentrated aqueous solutions of glyphosate salts. Moreover, certain surfactants can interact with other ingredients during the production process and rising up the viscosity of the herbicidal aqueous formulation. If the viscosity is too high, handling/production process of the concentrated herbicide can be difficult.

The addition of a large amount of glycol or an alcohol, up to 30%, can be used to avoid such problems in concentrated solutions of glyphosate and surfactant that are commercialized for later dilution on the field, as described in U.S. Pat. No. 5,385,750, which reference is incorporated herein by reference. However, this means that the resulting availability of the surface-active agent is reduced in the same proportion, which causes a lower efficiency of the final product. Also, the presence of the alcohols creates considerable drawbacks: they give strong odors and cause a noticeable lowering of the emulsifying ability of the surfactants. To overcome these problems, adjuvant surfactants are often used in tank mix, i.e. they are added separately from glyphosate to the final diluted herbicidal solution; even in this case some problems may occur, such as crystallization of the agrochemically active ingredient that may give clogging of the sprayer nozzles, especially when glyphosate is used in combination with other herbicides.

It is therefore well known to those skilled in the art that it is difficult to find a suitable surfactant with good bioefficacy and enhancing property for glyphosate; however, finding a suitable surfactant with good compatibility in addition to good bioefficacy and enhancing property is even more difficult.

It has now been discovered that an ethoxylated phospholipid-enriched soybean oil which is obtained by ethoxylating a soybean oil comprising from 5% to 30% by weight of phospholipids is highly effective as adjuvant for herbicidal compositions. The ethoxylated phospholipid-enriched soybean oil is compatible with other actives and common additives and does not show the crystallization problems that rise with many other surfactants.

SUMMARY OF THE INVENTION

In one aspect, the invention is an ethoxylated phospholipid-enriched soybean oil which is obtained by ethoxylating a soybean oil comprising from 5% to 30% by weight of phospholipids.

In another aspect, the invention is a herbicidal composition containing a herbicide and an ethoxylated phospholipid-enriched soybean oil which is obtained by ethoxylating a soybean oil comprising from 5% to 30% by weight of phospholipids.

In still another aspect, the invention is a method for killing or controlling the growth of weeds which includes applying on the fields an aqueous diluted herbicidal composition containing from 0.2 to 2% by weight a.e. of glyphosate and an ethoxylated phospholipid-enriched soybean oil which is obtained by ethoxylating a soybean oil comprising from 5% to 30% by weight of phospholipids, the weight ratio of glyphosate (a.e.) to the ethoxylated phospholipid-enriched soybean oil being from 1:1 to 50:1, in an amount sufficient to kill or control the growth of the weeds.

DESCRIPTION OF THE PREFERRED EMBODIMENTS

The glyphosate adjuvant of this invention may be prepared by ethoxylating a phospholipid-enriched soybean oil. Phospholipids naturally constitute about 1.5%-3.0% by weight of crude soybean oil. Phospholipid-enriched soybean oils are by-products of crude soybean oil processing.

Of the phospholipids in crude soybean oil, the best known and abundant are phosphatidylcholine (PC), phosphatidylethanolamine (PE) and phosphatidylinositol (PI). These phospholipids contain a diglyceride moiety, a phosphate group, and a simple organic molecule (choline, ethanolamine and inositol) that is connected to the phosphate group through an ester linkage. The hydrophilic head of the phospholipid contains the negatively charged phosphate group and relatively polar groups; the hydrophobic tail consists of fatty acid hydrocarbon chains.

When placed in water, phospholipids form a variety of structures depending on the specific properties of the phospholipid and they have, as such, emulsifying properties.

Noticeably, PE and PI contain hydroxyl and amino groups that can directly react with ethylene oxide to form hydrophilic polyoxyethylene chains that further increase their hydrophilic properties.

Pure phospholipids are solid at room temperature, but soluble in aliphatic and aromatic hydrocarbons, vegetable oil and animal fat, mineral oil and fatty acids.

Crude soybean oil, obtained by screw pressing and solvent extraction, exhibits a deposit of so-called gums on storage, whose chemical nature consists mainly of phospholipids (phosphatides), entrained oil and some other chemicals. Such gums are formed when the oil absorbs water that causes some of the phosphatides to become hydrated and thereby oil-insoluble.

Accordingly, "degumming", i.e. removing the gums from the oil, is a necessary step of the soybean oil refining process that prevents the formation of a gum deposit on storage. Degumming, which is commonly made by hydrating the crude oil and removing the hydrated gums from the oil, provides a supernatant phase of wet, refined oil and a phospholipid-enriched oil foot which is further dried, decolorized and possibly added with fluidity agents to provide concentrated phospholipids in oil. Water degumming is the oldest degumming oil treatment and forms the basis of the production of concentrated phospholipids, mainly known as "soybean lecithin", which is the most common commercial form of phospholipid-enriched soybean oil.

Commercial soybean lecithin consists not only of a mixture of phospholipids, but also of triglycerides and minor quantities of fatty acids, pigments, sterols and carbohydrates. Soybean lecithin typically comprises more than 60% by weight of phospholipids and is usually in solid form.

Phospholipid-enriched soybean oils containing far lower amounts of phospholipids are also available. Such phospholipid-enriched soybean oils may derive from the preparation of powdery soybean phospholipids from concentrated phospholipids, that usually takes place by solvent extraction, solvent fractionation, supercritical carbon dioxide extraction and ultrafiltration purification. Beside the high purity and non-off flavor powdery phospholipids, these processes give rise to abundant fractions of phospholipid-enriched soybean oil, containing various amounts of soybean triglycerides and phospholipids.

By way of example, fractions of oil enriched in phosphatidylcholine (PC-fractions) may be recovered by alcohol extraction because phosphatidylcholine is relatively more soluble in ethanol than the other phospholipids; these PC-fractions are especially appreciated in food applications, because they are choline-rich and less sensitive to browning on heating, but their production process leaves behind less appreciated fractions of PE- and PI-enriched soybean oil comprising lower amount of the phospholipid.

These fractions are suitable as raw material for the preparation, by ethoxylation, of the adjuvants according to this invention.

For the purposes of the present application, the expression "phospholipid-enriched soybean oil" means soybean oil comprising from 5% to 30% by weight of soybean phospholipids; the preferred phospholipid-enriched soybean oil used for the preparation of the adjuvant comprises from 5% to 15% by weight of soybean phospholipids, even more preferably about 10% by weight of phospholipids. According to a preferred embodiment, the phospholipid-enriched soybean oil useful for the preparation, by ethoxylation, of the adjuvant of the application is fluid at ambient temperature and pressure. The amount of soybean oil triglycerides in the phospholipid-enriched soybean oil that is ethoxylated is not critical, as long as the oil is fluid.

The fatty acid composition of the triglycerides is the one which is typical of soybean oil, which is mainly based of $C_{16}$ saturated and $C_{18}$ saturated, monounsaturated and polyunsaturated fatty acids, particularly of palmitic, stearic, oleic, linoleic and linolenic acid, with an iodine value of from about 120 to about 140. Advantageously the triglycerides represent at least 60% by weight, and even up to 85% by weight, of the phospholipid-enriched soybean oil that is ethoxylated. The ethoxylation of lecithin is known from U.S. Pat. No. 2,310,679, which is directed to an oxyalkylated lecithin and to a method of making the same, and which reference is incorporated herein by reference. According to U.S. Pat. No. 2,310,679 which is incorporated herein by reference, the oxyalkylation may take place in the presence of an inert solvent, such as a chlorinated hydrocarbon, xylene, a chlorinated ether, dioxane and the like.

It has now been found that the phospholipid-enriched soybean oil comprising from 5% to 30% of phospholipid can be ethoxylated without the presence of any inert solvent. The triglycerides that are contained in the phospholipid-enriched soybean oil, in fact, serve to render both the starting mixture and the final adjuvant liquid, which is highly appreciated in the conduct of the preparation process and for the final formulator or user. Even if the triglycerides compete with the phospholipids in the reaction with ethylene oxide, their presence does not negatively affect the performances of the adjuvant, in terms of compatibility and bioefficacy.

Accordingly, the ethoxylated phospholipid-enriched soybean oil useful as adjuvants of glyphosate compositions are obtained by reacting the phospholipid-enriched soybean oil with from 30 to 90% by weight, preferably from 50 to 70% by weight, of ethylene oxide at temperature between 90° C. and 180° C., in the presence of a basic catalyst, typically potassium hydroxide, at pressure comprised between 1 to 5 bar for 60 to 300 minutes.

Small amounts of glycerol, about 1 to 4% by weight, are advantageously added to the phospholipid-enriched soybean oil to facilitate the start of the reaction. The reaction conditions, especially the time and pressure, should be set in order to drive ethylene oxide to complete reaction.

The resulting ethoxylated phospholipid-enriched soybean oil thus incorporates from 30 to 90% by weight, preferably from 50 to 70% by weight, of units deriving from ethylene oxide.

The temperature is preferably maintained during the reaction below 170° C., preferably at about 160° C., in order to avoid excessive discoloration of the final adjuvant and decomposition of the phospholipids.

Along with the products formed from the direct ethoxylation of the phospholipids, the adjuvant of the invention comprises the ethoxylated derivatives of the soybean oil triglycerides: they are typically the mono- and di-esters of the fatty acids of soybean oil with poly(oxyethylene), ethoxylated glycerine and poly(oxyethylene)glycol. Some amounts of ethoxylated diglycerides and triglycerides are also formed, especially when the reaction temperature is maintained below 150° C.

The invention is further directed to herbicidal compositions containing a herbicide, which is preferably glyphosate, and the above described ethoxylated phospholipid-enriched soybean oil as adjuvant. Any water-soluble salt of glyphosate may be used in the herbicidal compositions according to the practice of this invention.

Glyphosate is an organic compound that contains three acidic protonable groups, and in its acid form is relatively insoluble in water. Therefore, glyphosate is normally formulated and applied as a water-soluble salt. Although monobasic, dibasic, and tribasic salts of glyphosate can be made, it has generally been preferred to formulate and apply glyphosate in the form of a monobasic salt, for example as a potassium or monoalkyl ammonium salt. Suitable salts include salts of isopropylamine; sodium; potassium; ammonium; mono-, di-, tri- and tetra-$C_{1-4}$-alkylammonium; mono-, di- and tri-$C_{1-4}$-alkanolammonium; mono-, di- and tri-$C_{1-4}$-alkylsulfonium; and sulfoxonium. Mixtures of salts can also be useful in certain formulations.

The preferred forms of glyphosate in the herbicidal compositions are the isopropylamine salt of glyphosate and the potassium salt of glyphosate. Beside the ethoxylated phospholipid-enriched soybean oil, as tank-mix or built-in adjuvant, and glyphosate, the herbicidal compositions of the invention may further contain, as further ingredients:

- other surfactants, such as cationic, anionic, non-ionic, and amphoteric surfactants, such as nonionic or anionic alkylpolyglycosides, alkoxylated fatty alcohols or amines, anionic esters of (alkoxylated) fatty alcohols, $C_6$-$C_{18}$ alkyldimethyl betaine.
- other herbicides, such as salts of glufosinate, bentazon, fomesafen, 2,4-D and its derivatives, dicamba, MCPA, MCPP, MCPB, paraquat, clopyralid, dichlorprop, imazalil, picloram, diquat, terbuthylazine, florasulam, isoproturon, diuron, diflufenican and mixtures thereof;
- other biocidally active ingredients or compositions, for example insecticides, fungicides, bactericides, acaracides, nematicides and/or plant growth regulators, in order to broaden the spectrum of activity;
- fertilizers (nitrogen source), such as ammonium sulfate, ammonia solutions, ammonium nitrate, ammonium hydrogen sulphate, ammonium acetate, ammonium formiate, ammonium oxalate, ammonium carbonate, ammonium hydrogen carbonate, ammonium thiosulfate, ammonium phosphate, diammonium hydrogen phosphate, ammonium dihydrogen phosphate, sodium ammonium hydrogen phosphate, ammonium thiocyanate, urea, thiourea and their blends;
- water soluble organic solvents, such as glycerol, ethylene glycol, propylenglycole, dipropylene glycol methyl ether (Dowanol DPM), dipropylene glycol, butyldiglycol, dimethylsulfoxide (DMSO), N-methyl-2-pyrrolidone, dibutoxymethane (butylal), methanol, ethanol, isopropanol, ethyl lactate (purasolv), propylene carbonate and mixture thereof;
- other usual additives of agrochemical compositions, such as antifoam agents, antifreeze agents, dyes, stabilizers, buffers, thickeners, flow enhancers, wetting agents, lubricants, fillers, drift control agents, stickers, evaporation retardants, preservatives and the like.

The use of ammonium sulphate as fertilizer in the herbicidal composition of the present invention is particularly suitable, because it enhances rapid uptake of glyphosate into plant foliage.

It is preferred that, when the composition of the invention contains additives, such additional components are environmentally friendly, substantially non-toxic to aquatic life, and have acceptable efficacy.

The herbicidal composition of the present invention may be a diluted, ready to use, spray aqueous solution, a concentrated aqueous composition, or a solid glyphosate composition. The term "diluted" references the amount of glyphosate in the solution; the solution is meant to be diluted if it contains no more than 2% by weight a.e. of glyphosate. Throughout the specification, unless otherwise indicated, the amounts of glyphosate and salts thereof are provided on an acid equivalent basis (a.e.).

In the preferred embodiment, the herbicidal composition of the present invention is therefore a herbicidal aqueous formulation, preferably a solution, possibly ready to use by spray application, that includes from 0.2% to 2% by weight a.e. of glyphosate, ethoxylated phospholipid-enriched soybean oil and, optionally, the further ingredients listed above, such as other active ingredients, fertilizers, solvents, micronutrients, surfactants and/or other additives commonly used in agrochemical compositions. Generally, the weight ratio of glyphosate (a.e.) to ethoxylated phospholipid-enriched soybean oil in the formulation is from about 1:1 to about 50:1, preferably from about 1:1 to about 20:1, most preferably from about 1:1 to about 10:1.

The herbicidal aqueous formulation of the invention is usually prepared by adding a concentrated, usually aqueous, glyphosate composition, that may or may not contain a surfactant, to about half weight of water, based on the final content of water in the solution, successively adding to the obtained solution the ethoxylated phospholipid-enriched soybean oil, the optional other ingredients and finally adding the remaining amount of water.

In another embodiment, the herbicidal composition of the invention is a concentrated aqueous herbicidal composition that typically contains from 100 to 600 g/l as acid equivalent of salts of glyphosate and from 1 to 50% by weight, preferably from 2 to 25% by weight, of the ethoxylated phospholipid-enriched soybean oil.

The concentrated aqueous herbicidal composition of the present invention comprises at least 10% by weight, preferably from 20 to 60% by weight, of water.

In some preferred embodiments, the concentrated aqueous herbicidal composition comprises from 300 to 550 g/l a.e. of salts of glyphosate.

The concentrated aqueous herbicidal composition of the present invention may generally be prepared by mixing glyphosate salt solutions together with the ethoxylated phospholipid-enriched soybean oil, and optionally the further ingredients listed above, in a suitable mixing vessel equipped with a stirring unit, such as a blender.

In a preferred embodiment, the concentrated aqueous herbicidal composition exhibits a Brookfield® viscosity at 25° C. of less than 1500 mPa·s and in particular below 300 mPa·s.

In still a different embodiment, the present invention is directed to concentrated herbicidal compositions of glyphosate or salts thereof that are solid (i.e. substantially dry) and comprise from about 20% to about 90% by weight of glyphosate (a.e.), preferably from 30% to 50% of glyphosate (a.e.), and from 5 to 50% by weight, preferably from 10 to 25% by weight, of ethoxylated phospholipid-enriched soybean oil.

Typically, these solid compositions are in the form of granules.

The further ingredients listed above may be present in the solid herbicidal composition, such as other herbicides and biocidally active ingredients, together with additional surfactants, fertilizers and usual additives.

In still another form, the present invention provides a method for killing or controlling the growth of weeds by applying on the fields a diluted aqueous herbicidal composition containing glyphosate and the adjuvant according to the present invention, the weight ratio of glyphosate (a.e.) to the ethoxylated phospholipid-enriched soybean oil being from 1:1 to 50:1, in an amount sufficient to kill or control the growth of the weeds. The herbicidal compositions of the present invention, as such or in diluted form, are typically applied as foliar non selective herbicide or in combination with a post-emergence herbicide.

The method of the present invention is useful for combating and/or preventing unwanted plants among crops of useful plants. The method of the invention is also suitable combating and/or preventing unwanted plants in place physically distinct from crop areas, e.g., non-crop lands, along unplanted roadsides or under power lines.

The Applicant has found that, in diluted aqueous spray formulations of glyphosate, the presence of ethoxylated phospholipid-enriched soybean oil can help the formation of a solution of glyphosate in water, prevents crystallization phenomena and considerably accelerates the penetration of active ingredient in the treated biological materials.

The following Examples serve to illustrate the bioefficacy of the herbicidal compositions according to the invention. A comparison is made with analogous compositions prepared from other surfactants that are known to efficiently perform as adjuvant in glyphosate compositions.

EXAMPLES

Preparation of Ethoxylated Phospholipid-Enriched Soybean Oil 835 g of phospholipid-enriched soybean oil containing about 10% by weight of phospholipids are reacted with 1261 g of ethylene oxide in the presence of potassium hydroxide as catalyst at 160° C. for about 240 minutes under a pressure of 1-5 bar, in the presence of 3% of glycerol.

The ethoxylated phospholipid-enriched soybean oil obtained is a liquid yellowish product (ETOLEC1).

Preparation of Ethoxylated Soybean Oil Enriched with Soybean Lecithin (Comparative).

835 g of soybean oil are reacted with 1261 g of ethylene oxide in the presence of potassium hydroxide as catalyst at 160° C. for about 240 minutes under a pressure of 1-5 bar, in the presence of 3% of glycerol. The resulting ethoxylated soybean oil is mixed with 10% by weight of soybean lecithin and a liquid yellowish product is obtained (MIXLEC1).

Bioefficacy Test (Greenhouse Tests)

ETOLEC1 was tested for bioefficacy in greenhouse trials using glyphosate based CPP (TouchDown Hi-Tech from Syngenta) at 4.8 oz/a on the following weeds: common barnyard and velvetleaf. The tank mix test was performed in comparison with MIXLEC1 and with two popular effective adjuvants: Liberate®, from Loveland Products, Inc. (US) and Induce®, from Helena Chemical Company (US). Liberate® is an adjuvant based on lecithin, methyl esters of fatty acids and alcohol ethoxylated. Induce®, according to its specimen label, is an adjuvant based on a blend of alkyl aryl polyoxyalkane ethers, fatty acids and dimethyl polysiloxane. The adjuvants were tested at 0.25%, 0.375% and 0.5% (v/v) on common barnyard and at 0.25%, 0.375% and 0.5% (v/v) on velvet leaf for a 7 days and 14 days treatments (respectively 7DAT and 14DAT) with 0.188 lb glyphosate (a.e.)/acre (a). The spray volume used was 15 gal/a applied through 8002 even flat fan nozzle for 4 replications. The results of the tests are reported as "% control" considering 0% as no control and 100% as total control of the weeds and they are showed in the following tables (Tables 1-6).

TABLE 1

% Control on common barnyard (0.25% v/v)

| | 7 DAT (%) | 14 DAT (%) |
|---|---|---|
| ETOLEC1 | 70.2 | 91.2 |
| MIXLEC1 | 65.5 | 78.8 |
| INDUCE ® | 60 | 64.7 |
| LIBERATE ® | 30 | 29.2 |

TABLE 2

% Control on common barnyard (0.375% v/v)

| | 7 DAT (%) | 14 DAT (%) |
|---|---|---|
| ETOLEC1 | 75.2 | 94.8 |
| MIXLEC1 | 70.5 | 85.5 |
| INDUCE ® | 65.8 | 60.5 |
| LIBERATE ® | 30.0 | 30.8 |

TABLE 3

% Control on common barnyard (0.5% v/v)

| | 7 DAT (%) | 14 DAT (%) |
|---|---|---|
| ETOLEC1 | 79.3 | 95.2 |
| INDUCE ® | 70.5 | 72.5 |
| LIBERATE ® | 37.5 | 31.7 |

TABLE 4

% Control on velvetleaf (0.25% v/v)

| | 7 DAT (%) | 14 DAT (%) |
|---|---|---|
| ETOLEC1 | 68.8 | 88.2 |
| MIXLEC1 | 60.5 | 75.8 |
| INDUCE ® | 70.3 | 86.7 |
| LIBERATE ® | 61 | 79.8 |

TABLE 5

| % Control on velvetleaf (0.375% v/v) | | |
|---|---|---|
| | 7 DAT (%) | 14 DAT (%) |
| ETOLEC1 | 70.8 | 88.7 |
| MIXLEC1 | 63.5 | 81.7 |
| INDUCE ® | 68.5 | 82.2 |
| LIBERATE ® | 59.2 | 72.7 |

TABLE 6

| % Control on velvetleaf (0.5% v/v) | | |
|---|---|---|
| | 7 DAT (%) | 14 DAT (%) |
| ETOLEC1 | 68.3 | 86.3 |
| INDUCE ® | 69.3 | 83.5 |
| LIBERATE ® | 60.5 | 71.3 |

The tests show that the adjuvant according to the invention shows improved efficacy compared to commercial products in all 14DAT tests and in most 7DAT tests.

What is claimed is:

1. A herbicidal composition comprising a herbicide and an ethoxylated phospholipid-enriched soybean oil wherein the ethoxylated phospholipid-enriched soybean oil is prepared using a method comprising ethoxylating a soybean oil comprising from about 5% to about 30% by weight of phospholipids.

2. The herbicidal composition of claim 1 wherein the herbicide is glyphosate.

3. The herbicidal composition of claim 2 wherein the weight ratio of glyphosate (a.e.) to the ethoxylated phospholipid-enriched soybean oil is from 1:1 to 50:1.

4. The herbicidal composition of claim 3 wherein the herbicidal composition is an aqueous formulation comprising from about 0.2 to about 2% by weight a.e. of glyphosate.

5. The herbicidal composition of claim 2 wherein the herbicidal composition is an aqueous composition comprising from 100 g/l to 600 g/l a.e. of glyphosate salts and from 1% to 50% by weight of the ethoxylated phospholipid-enriched soybean oil.

6. The herbicidal composition of claim 2 wherein the herbicidal composition is a solid composition and comprises from 20% to 90% by weight of glyphosate (a.e.) and from 5% to 50% by weight of ethoxylated phospholipid-enriched soybean oil.

7. A method for killing or controlling growth of weeds comprising applying on fields an aqueous diluted herbicidal composition having from about 0.2 to about 2% by weight a.e. glyphosate and an ethoxylated phospholipid-enriched soybean oil wherien the ethoxylated phospholipid-enriched soybean oil is prepared using a process comprising ethoxylating a soybean oil comprising from about 5% to about 30% by weight phospholipids, the weight ratio of glyphosate (a.e.) to the ethoxylated phospholipid-enriched soybean oil being from 1:1 to 50:1, in an amount sufficient to kill or control the growth of the weeds.

* * * * *